(12) United States Patent
Grill et al.

(10) Patent No.: US 10,702,696 B2
(45) Date of Patent: Jul. 7, 2020

(54) SYSTEMS AND METHODS FOR SPINAL CORD STIMULATION

(71) Applicant: Duke University, Durham, NC (US)

(72) Inventors: Warren M. Grill, Durham, NC (US); Tianhe Zhang, Durham, NC (US)

(73) Assignee: Duke University, Durham, NC (US)

( * ) Notice: Subject to any disclaimer, the term of this patent is extended or adjusted under 35 U.S.C. 154(b) by 10 days.

(21) Appl. No.: 15/806,686

(22) Filed: Nov. 8, 2017

(65) Prior Publication Data

US 2018/0064943 A1 Mar. 8, 2018

Related U.S. Application Data

(63) Continuation of application No. PCT/US2016/031166, filed on May 6, 2016.

(60) Provisional application No. 62/158,731, filed on May 8, 2015.

(51) Int. Cl.
*A61N 1/36* (2006.01)
*A61N 1/05* (2006.01)
*A61N 1/372* (2006.01)
*A61B 5/00* (2006.01)

(52) U.S. Cl.
CPC ....... *A61N 1/36062* (2017.08); *A61N 1/0551* (2013.01); *A61N 1/36071* (2013.01); *A61N 1/36167* (2013.01); *A61N 1/37247* (2013.01); *A61B 5/4824* (2013.01)

(58) Field of Classification Search
CPC ............ A61N 1/36062; A61N 1/37247; A61N 1/36167; A61N 1/36071; A61N 1/0551; A61B 5/4824
See application file for complete search history.

(56) References Cited

U.S. PATENT DOCUMENTS 5,643,330 A * 7/1997 Holsheimer ......... A61N 1/0551
607/117
7,606,623 B2 * 10/2009 Ludlow .............. A61N 1/36007
607/62

(Continued)

FOREIGN PATENT DOCUMENTS

CA 2837225 A1 12/2012
WO 2014159880 A1 10/2014

OTHER PUBLICATIONS

CIPO, Examination report for Canadian Patent Application No. 2,958,218, dated Nov. 23, 2017.

(Continued)

*Primary Examiner* — Amanda K Hulbert
*Assistant Examiner* — Natasha Patel
(74) *Attorney, Agent, or Firm* — NK Patent Law

(57) ABSTRACT

Delivering stimulation includes delivering temporal patterns of stimulation pulses to respective transducers of an array of transducers, wherein the delivery of the pattern to a particular transducer of the array is different from at least some of the deliveries of the patterns to the other transducers of the array at least according to a time delay. The patterns delivered may include regular temporal patterns each having a respective constant inter-pulse interval. The constant inter-pulse intervals may be about the same. The patterns may be staggered. The transducers may deliver electrical, optical, acoustic, thermal or magnetic stimulation.

22 Claims, 11 Drawing Sheets

(56) References Cited

U.S. PATENT DOCUMENTS

2002/0188331 A1* 12/2002 Fang .................. A61N 1/08
    607/48
2006/0149337 A1    7/2006 John
2011/0029040 A1    2/2011 Walker et al.
2011/0040348 A1* 2/2011 Wacnik .............. A61N 1/36071
    607/46
2013/0231715 A1    9/2013 Grill, Jr. et al.
2014/0350634 A1* 11/2014 Grill ................ A61N 1/36067
    607/45

OTHER PUBLICATIONS

EPO, Extended European Search Report in European Patent Application No. 16793243.3 dated Nov. 15, 2018.
Australian Government—IP Australia, Examination Report in Australian Application No. 2016261228 dated Feb. 7, 2020.

* cited by examiner

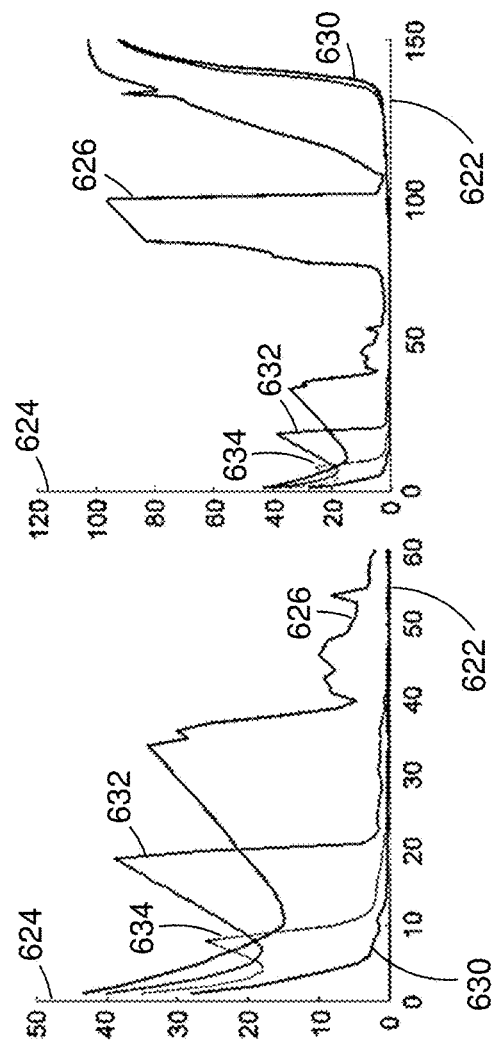
FIG. 6C
FIG. 6B
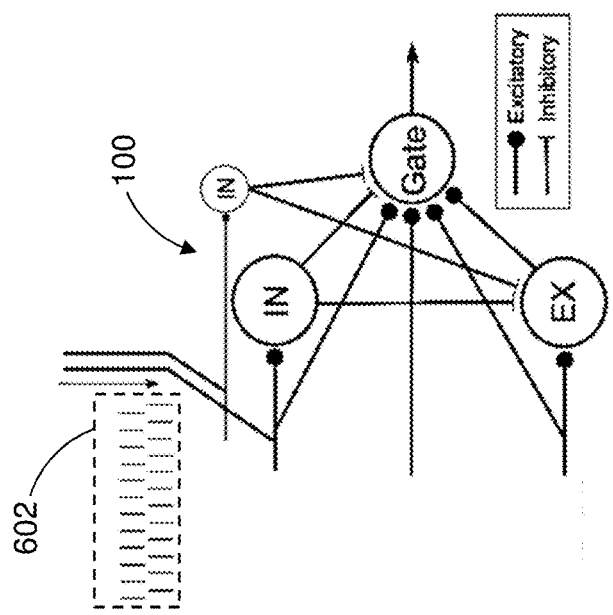
FIG. 6A

SYSTEMS AND METHODS FOR SPINAL CORD STIMULATION

CROSS-REFERENCE TO RELATED APPLICATION

This application claims the benefit of priority of PCT patent application no. PCT/US16/31166 filed on May 6, 2016, which claims the benefit of U.S. provisional patent application No. 62/158,731 titled "SYSTEMS AND METHODS FOR SPINAL CORD STIMULATION," filed on May 8, 2015, which is incorporated herein in its entirety by this reference.

TECHNICAL FIELD

The presently disclosed subject matter relates to spinal cord stimulation, and more specifically, to administering asynchronous spinal cord stimulation (SCS) based on temporal patterns of electrical stimulation.

BACKGROUND

Spinal cord stimulation (SCS) has emerged as a viable means of managing chronic pain when conventional therapies, such as pharmaceuticals and surgery, have not been effective. However, the clinical success of SCS has been highly variable and success rates have not improved with time. Conventional clinical SCS, which involves the synchronized delivery of stimulation at a single frequency to all dorsal column fibers originating from the source of pain, both excites and inhibits sensory neurons responsible for relaying nociceptive information to the brain. SCS should inhibit the activity of these neurons to produce a beneficial effect, as sensory neuron activity correlates with perceived pain, but higher frequencies of stimulation, and as a result greater power consumption, are required to overcome neuronal excitation by conventional SCS. Higher frequencies of SCS require more power and may be accompanied by side-effect paresthesias, or tingling sensations associated with neural activation of the dorsal columns and other sensations, that may be intense enough to produce less favorable clinical outcomes.

Asynchronous activation has been proposed as a possible mechanism by which "burst" and "high or kilohertz frequency" SCS exert pain relief without paresthesia, but the parameters used in burst and high frequency SCS are not necessarily optimized for efficacy or efficiency. While some SCS devices may be capable of indirectly producing asynchronous activation of dorsal column fibers through high-frequency (>1.5 kHz) stimulation via multiple electrode contacts, model-based design and direct application of multiple asynchronous (e.g., staggered or random) patterns of SCS at average frequencies in the range of standard frequencies of clinical SCS to produce pain relief have not been explored or previously described.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a method of delivering electrical stimulation includes: delivering temporal patterns of electrical stimulation pulses to respective electrodes of an array of electrodes, wherein the delivery of the pattern to a particular electrode of the array is different from at least some of the deliveries of the patterns to the other electrodes array at least according to a time delay.

In at least one example, at least some of the patterns delivered include regular temporal patterns each having a respective constant inter-pulse interval.

In at least one example, the constant inter-pulse intervals are about the same.

In at least one example, the time delay is approximately a percentage of the constant inter-pulse intervals.

In at least one example, at least some of the patterns delivered differ from others of the patterns delivered only by the time delay such that the patterns are staggered.

In at least one example, the deliveries of at least some of the patterns delivered differ from others of the patterns delivered according to time delays that vary.

In at least one example, at least some of the patterns delivered include non-regular temporal patterns each having respective varying inter-pulse intervals.

In at least one example, at least some of the patterns delivered differ from others of the patterns delivered only by the time delay such that the patterns are staggered.

In at least one example, at least some of the patterns delivered include regular temporal patterns each having a respective constant inter-pulse interval; and at least some of the patterns delivered include non-regular temporal patterns each having respective varying inter-pulse intervals.

In at least one example, at least some of the patterns delivered differ from others of the patterns delivered only by the time delay such that the patterns are staggered.

In at least one example, at least some of the patterns delivered are non-regular temporal patterns each having respective varying random inter-pulse intervals drawn from a distribution.

In at least one example, at least some of the patterns delivered are about the same.

In at least one example, a remote control device at least intermittently provides temporal pulse pattern programming; and a stimulation device is connected to or in communication with the array of electrodes receives the temporal pulse pattern programming from the remote control device and delivers the temporal patterns of electrical stimulation pulses to the electrodes according to the temporal pulse pattern programming.

In at least one example, the remote control device is configured to generate the temporal pulse pattern programming.

In at least one example, the remote control device is configured to receive and store the temporal pulse pattern programming.

According to at least one embodiment, a system for delivering electrical pulse stimulation includes: a control device configured to at least intermittently provide temporal pulse pattern programming; and a stimulation device including a control module, multiple electrodes in electrical communication with the control module, and an input device in at least intermittent communication with the control device to receive the temporal pulse pattern programming, the stimulation device configured to deliver respective temporal patterns of electrical stimulation pulses to the multiple electrodes according to the temporal pulse pattern programming, wherein the temporal pulse pattern programming includes instructions to deliver via different electrodes of the array respective temporal patterns that differ at least according to a time delay.

In at least one example, the temporal pulse pattern programming includes instructions such that at least some of the patterns delivered include regular temporal patterns each having a respective constant inter-pulse interval.

In at least one example, the temporal pulse pattern programming includes instructions such that at least some of the patterns delivered differ from others of the patterns delivered only by the time delay such that the patterns are staggered.

In at least one example, the temporal pulse pattern programming includes instructions such that the deliveries of at least some of the patterns delivered differ from others of the patterns delivered according to time delays that vary.

In at least one example, the temporal pulse pattern programming includes instructions such that at least some of the patterns delivered include non-regular temporal patterns each having respective varying inter-pulse intervals.

In at least one example, the temporal pulse pattern programming includes instructions such that at least some of the patterns delivered differ from others of the patterns delivered only by the time delay such that the patterns are staggered.

In at least one example, the temporal pulse pattern programming includes instructions such that: at least some of the patterns delivered include regular temporal patterns each having a respective constant inter-pulse interval; and at least some of the patterns delivered include non-regular temporal patterns each having respective varying inter-pulse intervals.

In at least one example, the temporal pulse pattern programming includes instructions such that at least some of the patterns delivered differ from others of the patterns delivered only by the time delay such that the patterns are staggered. In at least one example, the temporal pulse pattern programming includes instructions such that at least some of the patterns delivered are non-regular temporal patterns each having respective varying random inter-pulse intervals drawn from a distribution.

In at least one example, the temporal pulse pattern programming includes instructions such that at least some of the patterns delivered are about the same.

In at least one example, the control device includes a remote control device configured to at least intermittently wirelessly transmit temporal pulse pattern programming, and the input device of the stimulation device at least intermittent communicates wirelessly with the remote control device to receive the temporal pulse pattern programming.

In at least one example, the remote control device and the stimulation device communicate through at least one of: radiofrequency (RF) transmission; Bluetooth transmission; optical transmission; and a wireless local area network (WLAN).

In at least one example, the remote control device is configured to generate the temporal pulse pattern programming.

In at least one example, the remote control device is configured to receive and store the temporal pulse pattern programming.

According to at least one embodiment, a remote control device is configured to at least intermittently provide temporal pulse pattern programming to a stimulation device that is connected to or in communication with an array of electrodes and delivers temporal patterns of electrical stimulation pulses to the electrodes according to the temporal pulse pattern programming, wherein the temporal pulse pattern programming includes instructions to deliver, via different electrodes of the array, respective temporal patterns that differ at least according to a time delay.

In at least one example, the remote control device includes a computer, an electronic tablet, or a smartphone.

In at least one embodiment, a method of delivering stimulation includes: delivering temporal patterns of stimulation pulses to respective transducers of an array of transducers, wherein the delivery of the pattern to a particular transducer of the array is different from at least some of the deliveries of the patterns to the other transducers of the array at least according to a time delay.

In at least one example, the array of transducers includes electrodes.

In at least one example, the array of transducers includes optical transducers.

In at least one example, the array of transducers includes acoustic transducers.

In at least one example, the array of transducers includes thermal transducers.

In at least one example, the array of transducers includes magnetic transducers.

In various above embodiments, at least some of the patterns delivered are non-regular temporal patterns each having respective varying random inter-pulse intervals drawn from a distribution.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 6A is a schematic depicting simulation of staggered SCS delivered to the computational model 100 of FIG. 1

FIG. 6B is a plot comparison of SCS frequency vs. Gate neuron output relationships.

FIG. 6C is a plot comparison of SCS frequency vs. Gate neuron output relationships as in FIG. 6B over a larger SCS frequency range.

DETAILED DESCRIPTIONS

Figure 1:
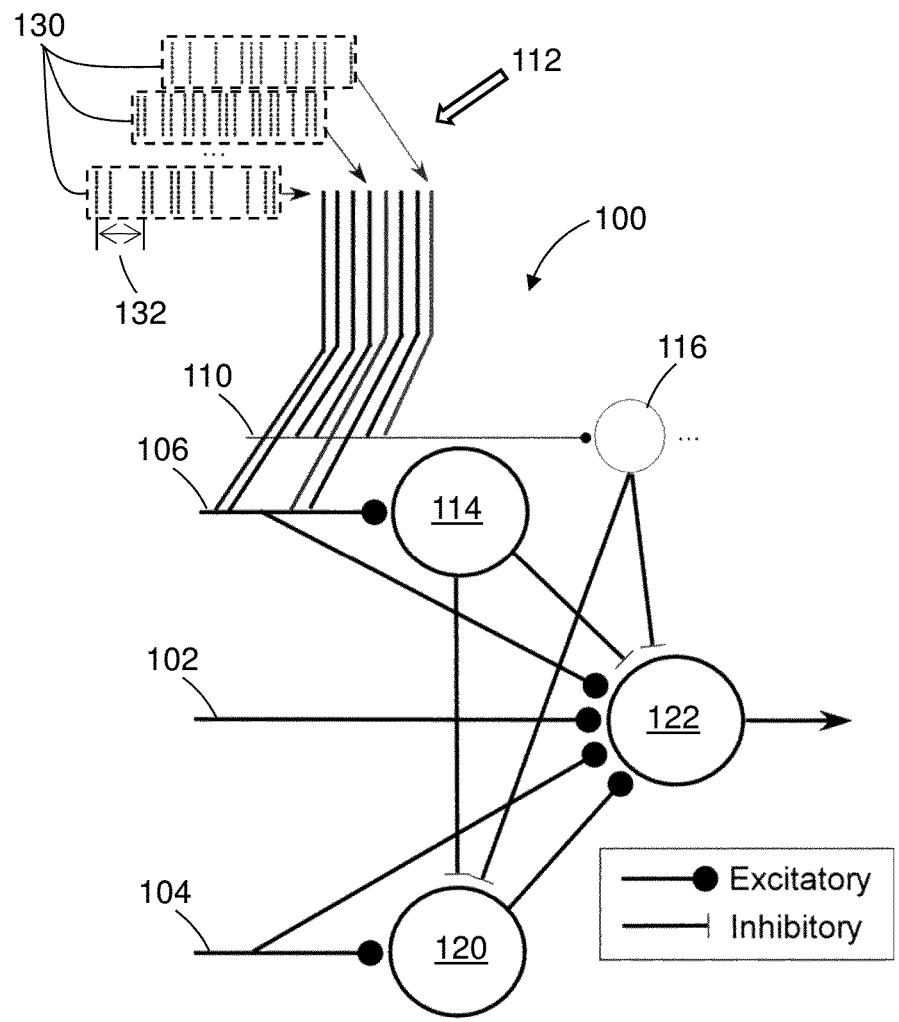
FIG. 1 is a schematic representation of a computational model used for model-based design and evaluation of temporal patterns of spinal cord stimulation (SCS) according to at least one embodiment.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

These descriptions relate to the use of asynchronous activation of dorsal column fibers to inhibit the activity of neurons, and thereby improve the efficacy of therapy, at stimulation frequencies comparable to or lower than current clinical standard frequencies (30 Hz-80 Hz). The below describes novel spatiotemporal patterns of SCS that suppresses the transmission of nociceptive information from the spinal cord more effectively than conventional SCS and at lower effective frequencies than conventional SCS. These features make the novel patterns more effective and efficient than conventional methods, and devices and algorithms using this method may thereby improve patient quality of life.

One embodiment includes staggering the timing of the pulse trains delivered at the same frequency to multiple, distinct populations of dorsal column fibers ("staggered SCS"). Another embodiment includes staggering "random SCS," which involves the delivery of different randomized patterns of stimulation to all dorsal column fibers or distinct or overlapping subpopulations of dorsal column fibers. Randomized patterns can be characterized by random inter-pulse intervals drawn from a distribution. Random SCS does not have to be staggered, though it can be, according to various embodiments.

A computational model of pain is used to reduce asynchronous SCS to practice in at least one embodiment. FIG. 1 is a representation of a computational model 100 for use in designing, evaluating, or optimizing temporal stimulation patterns according to at least one embodiment. The model 100 includes a network of simulated biophysical neurons that are connected in a manner consistent with existing schemes of the dorsal horn pain processing network as represented in FIG. 1. Inputs to the model include thirty Aβ fibers, fifteen Aδ fibers 102 and thirty C primary afferent fibers 104 that convey information from the periphery. The thirty Aβ fibers are divided into two sub-populations of fifteen fibers each, with one population of Aβ fibers 106 originating from the "local" source of pain and the other Aβ fibers 110 originating from a "surrounding" receptive field. SCS 112 will be delivered to the network via collaterals of the Aβ fibers to simulate dorsal column fiber activation via spinal cord stimulation.

Multiple A/C fibers and excitatory interneurons are used to account for the effect of temporal summation on neuronal activity as well as to add variability to the inputs. To simulate realistic signal propagation from a peripheral or dorsal column nerve fiber, propagation delays based on the conduction velocities of A and C fibers are incorporated into all inputs for all simulations. The assumed distance between the SCS electrode and the dorsal column network will be based on clinical placements of SCS electrodes relative to the target dermatome corresponding to the source of pain. Staggered or random SCS pulse trains are delivered to individual or distinct or overlapping groups within the Aβ-fiber collaterals including the inputs affected by SCS.

The model 100 includes inhibitory interneurons 114 and 116, an excitatory interneuron 120, and a gate or output neuron 122. Circular synapses denote excitatory connections. Flat synapses denote inhibitory connections. In asynchronous SCS two or more patterns 130 (up to arbitrary n) are delivered to distinct groups of fibers or individual fibers or overlapping fibers via the local and surround Aβ-fiber inputs 106 and 110, and distinct pulse trains are delivered to local and surround inputs when possible. SCS propagation distances will be set according to known clinical and/or patient-specific values. A time interval 132 of one hundred milliseconds represents the time scale in the patterns 130.

Figure 2:
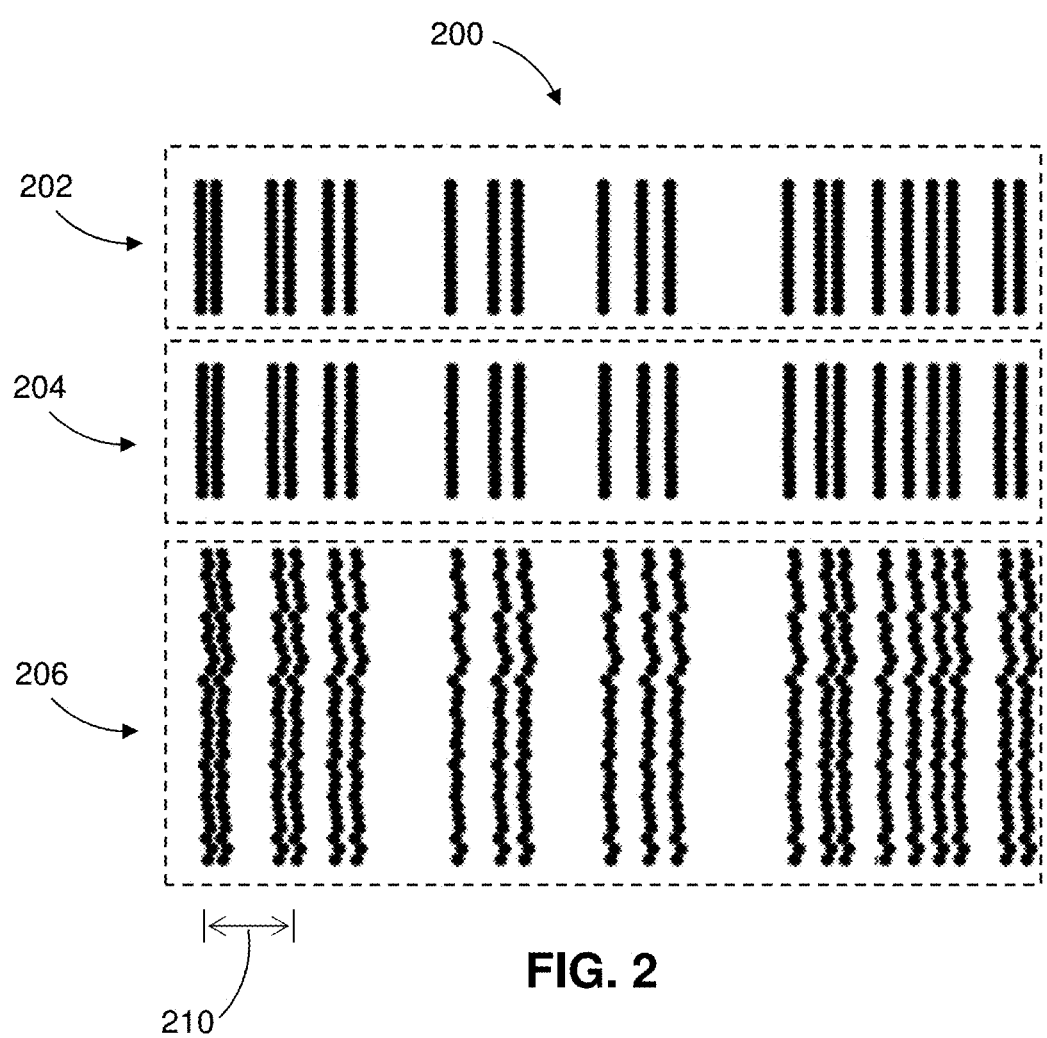
FIG. 2 is a twenty-second sample of ongoing inputs from peripheral afferent fibers that occur concurrently with SCS.

FIG. 2 is a twenty-second sample 200 of ongoing inputs from peripheral afferent fibers (fifteen Aβ inputs 202, fifteen Aδ inputs 204, thirty C inputs 206) that occur before SCS, concurrently with SCS, and after SCS. Each black dot on the graph represents a time point at which a spike is registered by a corresponding input to the model. A two-second interval 210 represents the time scale in FIG. 2. The time scale and sample duration of twenty seconds are examples only. Duration of an input need not be twenty seconds.

Figure 3B:
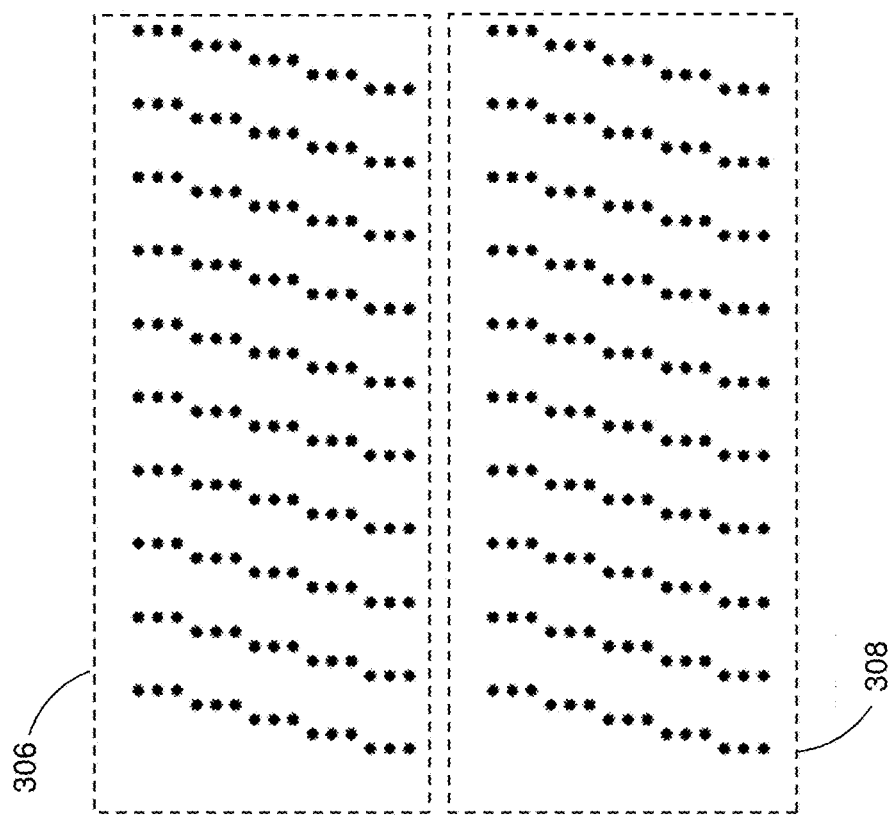
FIG. 3B shows examples of pulse train combinations delivered to local inputs of FIG. 1 and pulse train combinations delivered to surround inputs of FIG. 1 during staggered SCS.
Figure 3A:
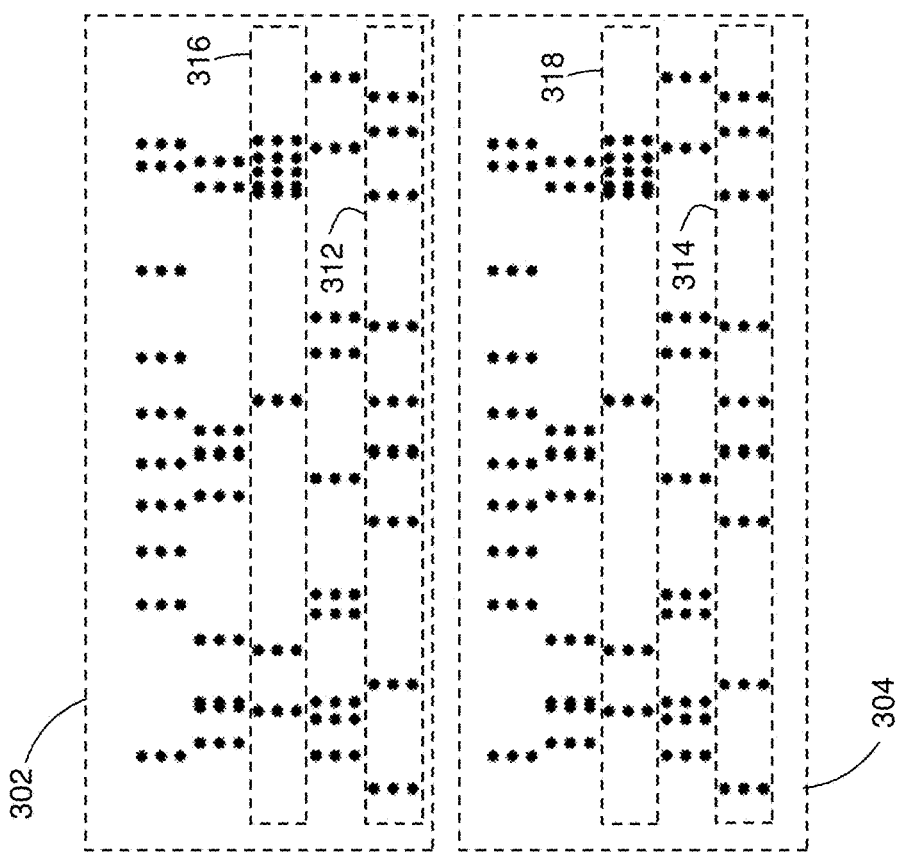
FIG. 3A shows examples of pulse train combinations delivered to local inputs of FIG. 1 and pulse train combinations delivered to surround inputs of FIG. 1 during random SCS.

FIG. 3A shows examples of pulse train combinations 302 delivered to fifteen local inputs (FIG. 1) and pulse train combinations 304 delivered to fifteen surround inputs (FIG. 1) during random SCS. FIG. 3B shows examples of pulse train combinations 306 delivered to fifteen local inputs (FIG. 1) and pulse train combinations 308 delivered to fifteen surround inputs (FIG. 1) during staggered SCS. In FIG. 3A, random SCS consists of one-second repeats of randomly generated sequences of pulses, all at the same average frequency (10 Hz shown). An equal number of local and surround inputs (FIG. 1) receives each randomized pulse train. For example, pulses 312 (FIG. 3) are delivered to local Aβ-fiber inputs 106 (FIG. 1), pulses 314 (FIG. 3) are delivered to surround Aβ-fiber inputs 110 (FIG. 1), pulses 316 (FIG. 3) are delivered to local Aβ-fiber inputs 106 (FIG. 1), and pulses 318 (FIG. 3) are delivered to surround Aβ-fiber inputs 110 (FIG. 1).

In FIG. 3B, staggered SCS consists of constant inter-pulse interval (IPI) pulse trains "staggered" relative to each other by fractions of the IPI (five groups, 20%×IPI stagger shown). In the example shown, all pulse trains are set to the same equivalent frequency (10 Hz), but this does not necessarily have to be the case, for example as in FIGS. 7A and 7B.

Figure 4:
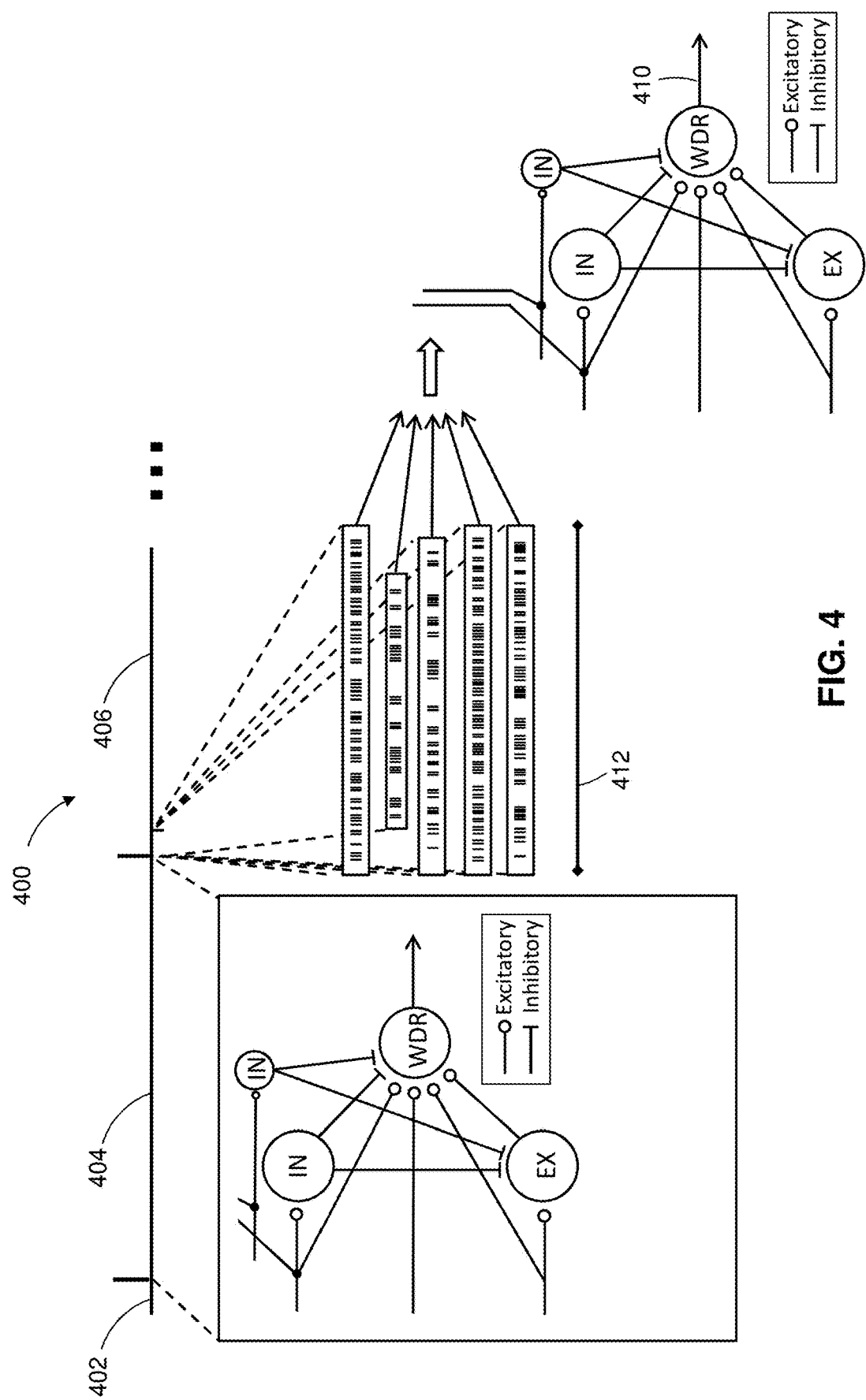
FIG. 4 is a timeline of computational simulations of asynchronous SCS according to at least one embodiment.

Computational simulations of asynchronous SCS are conducted as shown in FIG. 4 according to at least one embodiment. A brief simulation time interval 402, for example one second, elapses to allow the model to initialize, and peripheral sensory input consisting of a random spike train generated using a Poisson process whose characteristics matching those taken from the firing behavior of a peripheral neuroma are delivered to all Aβ, Aδ, and C-fiber inputs for the duration of the simulation. In random SCS, SCS using one-second repeats of randomly generated pulse trains are delivered to individual SCS inputs or distinct groups of SCS inputs for a time interval 406, for example twenty seconds commencing after the start of the peripheral input (FIG. 3A). In staggered SCS, fixed inter-pulse interval (IPI) pulse trains at a single frequency are applied to all SCS inputs, but pulse trains between inputs may be offset from each other (i.e. "staggered") by percentages of the full IPI (FIG. 3B). The output of the Gate neuron is recorded during staggered and random SCS, and the change in firing rate of the Gate neuron is used as the outcome measure, as the firing rate of the Gate neuron correlates with pain intensity. A set of fixed frequency controls, wherein the output of the WDR neuron in response to synchronized constant frequency SCS (cfSCS) from 1-150 Hz is used for comparison, as current SCS protocols use cfSCS.

FIG. 4 is a timeline 400 of each experimental run. SCS is delivered (time interval 406) following a brief model initialization period (time interval 402) and twenty seconds of conditioning stimulation (interval 404) using synchronized or randomized inputs similar to those recorded from neuromas in live preparations. The output 410 of the WDR neuron output (pain) is tracked as the outcome measure. The time band 412 represents a repeated time interval, for example a one-second time interval repeated twenty times.

Asynchronous SCS, implemented as random SCS and staggered SCS, may be more effective at suppressing Gate neuron behavior than cfSCS and can produce inhibition at lower frequencies than required by single frequency SCS through testing of an algorithm using a computational model of pain.

Figure 5B:
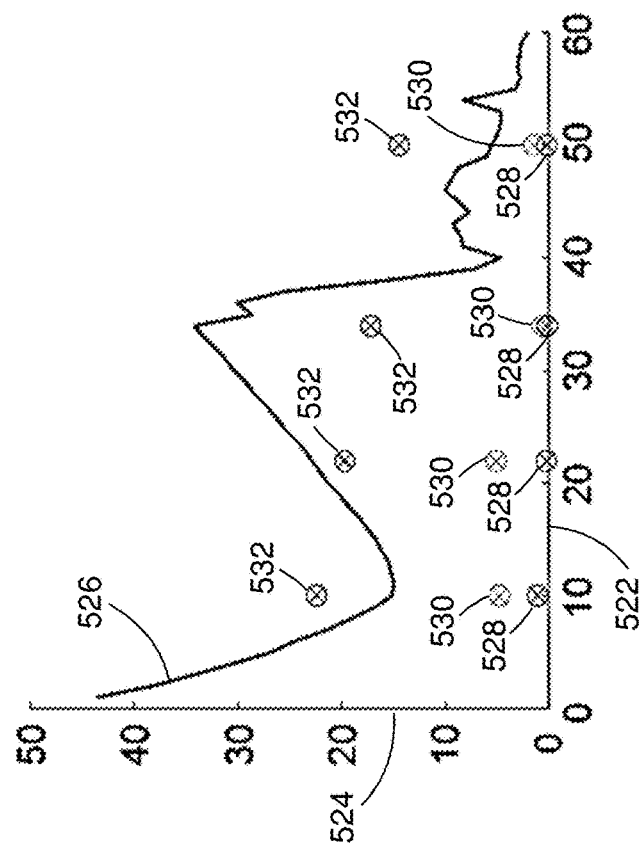
FIG. 5B is a plot comparison of SCS frequency vs. Gate neuron output relationships.
Figure 5A:
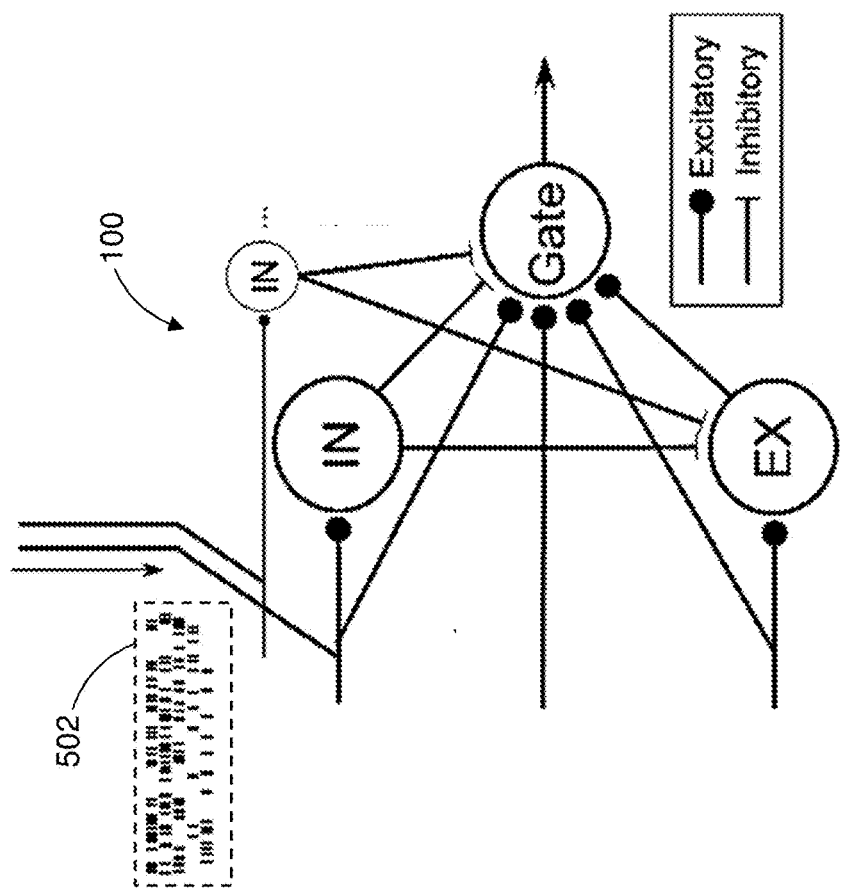
FIG. 5A is a schematic depicting simulation of random SCS delivered to the computational model of FIG. 1.

As shown in FIGS. 5A and 5B, the application of random SCS trains, with each pulse train set to at average frequencies of 10 Hz, 22 Hz, 34 Hz, and 50 Hz, inhibits the activity of the Gate neuron more than the inhibition produced by cfSCS. When two random trains are delivered to two distinct groups of fibers, random SCS suppresses the activity of the Gate neuron below its firing rate prior to the onset of SCS (47.8 spikes/s). Random SCS at 10 Hz and 50 Hz SCS excites the Gate neuron relative to cfSCS by 7.3 spikes/s and 8.9 spikes/s, respectively, while random SCS at 22 Hz and 34 Hz inhibits the Gate neuron relative to cfSCS by 3.2 spikes/s, and 17.1 spikes/s, respectively. Delivering random SCS to more distinct or overlapping groups of smaller populations of SCS inputs may improve the effects of random SCS. When 5 distinct random SCS pulse trains are delivered to 10 SCS inputs each, random SCS suppresses the firing rate of the Gate neuron to below 5.1 spikes/s in all cases and produces greater inhibition of the Gate neuron by 10.3 spikes/s, 17.8 spikes/s, 33.6 spikes/s, and 4.1 versus cfSCS at 10 Hz, 22 Hz, 34 Hz, and 50 Hz, respectively. When 10 groups of 3 fibers each receive random SCS or when all 30 SCS inputs receive a distinct random SCS pulse train, the firing rate of the Gate neuron never exceeds 1.3 spikes/s and random SCS produces substantially greater inhibition than cfSCS across all tested SCS frequencies (FIG. 5B).

FIG. 5A is a schematic depicting simulation of random SCS delivered to the computational model 100 of FIG. 1. Distinct random pulse trains 502 are all set to 10 pulses/s, 22 pulses/s, 34 pulses/s, or 50 pulses/s and are all set to the same pulse rate within a simulation. Trains 502 are applied to individual or distinct groups of dorsal column collaterals of Aβ fibers during an on-going peripheral input (example: multiple groups: 5× random corresponding to data points 530 in FIG. 5B; and 2× random corresponding to data points 532. No dorsal column input receives the same pattern as another.

FIG. 5B is a plot comparison of SCS frequency (axis 522 in Hz) vs. Gate neuron output (axis 524 in spikes/second) relationships at 10 pulses/s, 22 pulses/s, 34 pulses/s, and 50 pulses/s produced by conventional SCS (plot 526) and random SCS at equivalent average frequencies, denoted by the number of distinct groups of inputs receiving distinct random trains (data points 528).

At some stimulation frequencies, staggered SCS is more effective at suppressing WDR neuronal activity versus single frequency stimulation (FIGS. 6A-6C). When two pulse trains of equal frequencies are staggered by 0.5× the IPI corresponding to the stimulation frequency and delivered to two distinct groups of SCS inputs, staggered SCS outperforms cfSCS at stimulation frequencies exceeding 20 Hz. When three pulse trains of equal frequencies, delivered to three groups of SCS inputs, are staggered relative to each other by 0.33× the IPI, staggered SCS out-performs cfSCS at all frequencies exceeding 10 Hz. When five pulse trains, delivered to 5 groups of SCS inputs, are staggered relative to each other by 0.2× the IPI, staggered SCS outperforms cfSCS at all frequencies between 1 and 150 Hz SCS (FIG. 6B). Staggered SCS also reduces the variability or "jaggedness" in the frequency response relationship observed during cfSCS at higher SCS frequencies. The latter finding suggests that staggered SCS can be used to expand the parameter space over which SCS is effective (FIG. 6C) and make the outcomes of SCS less sensitive to the selection of particular values of stimulation parameters.

Although cfSCS at >35 Hz could produce inhibition comparable to that produced by random SCS, that random SCS and staggered SCS could both produce substantial inhibition of the Gate neuron at lower effective frequencies also suggests that asynchronous is more efficient than cfSCS. In addition, the effects of both random and staggered SCS depend on the number of groups receiving distinct random pulse trains, thus controlling the number of asynchronous pulse trains to be delivered and the input distributions affected by these pulse trains represents methods to customize and optimize therapy by random SCS.

FIG. 6A is a schematic depicting simulation of staggered SCS delivered to the computational model 100 of FIG. 1. Pulse trains 602 of equal frequency staggered relative to each other by a constant fraction of the inter-pulse interval (IPI) corresponding to the stimulation frequency (example: 0.5×IPI) are applied to distinct populations of dorsal column collaterals of Aβ fibers during on-going peripheral input. Propagation distance was set to 1 cm.

FIGS. 6B and 6C show distinct responses to staggered SCS. FIG. 6B is a plot comparison of SCS frequency (axis 622 in Hz) vs. Gate neuron output relationships (axis 624 in spikes/second) produced by conventional (plot 626) and staggered (plot 630) SCS, denoted by the number of distinct groups of inputs receiving distinctly staggered pulse trains: two groups corresponding to data points 632; three groups corresponding to data points 634; five groups corresponding to data points 630. FIG. 6C is a plot comparison of SCS frequency vs. Gate neuron output relationships as in FIG. 6B over a larger SCS frequency range (1-150 Hz).

Figure 7A:
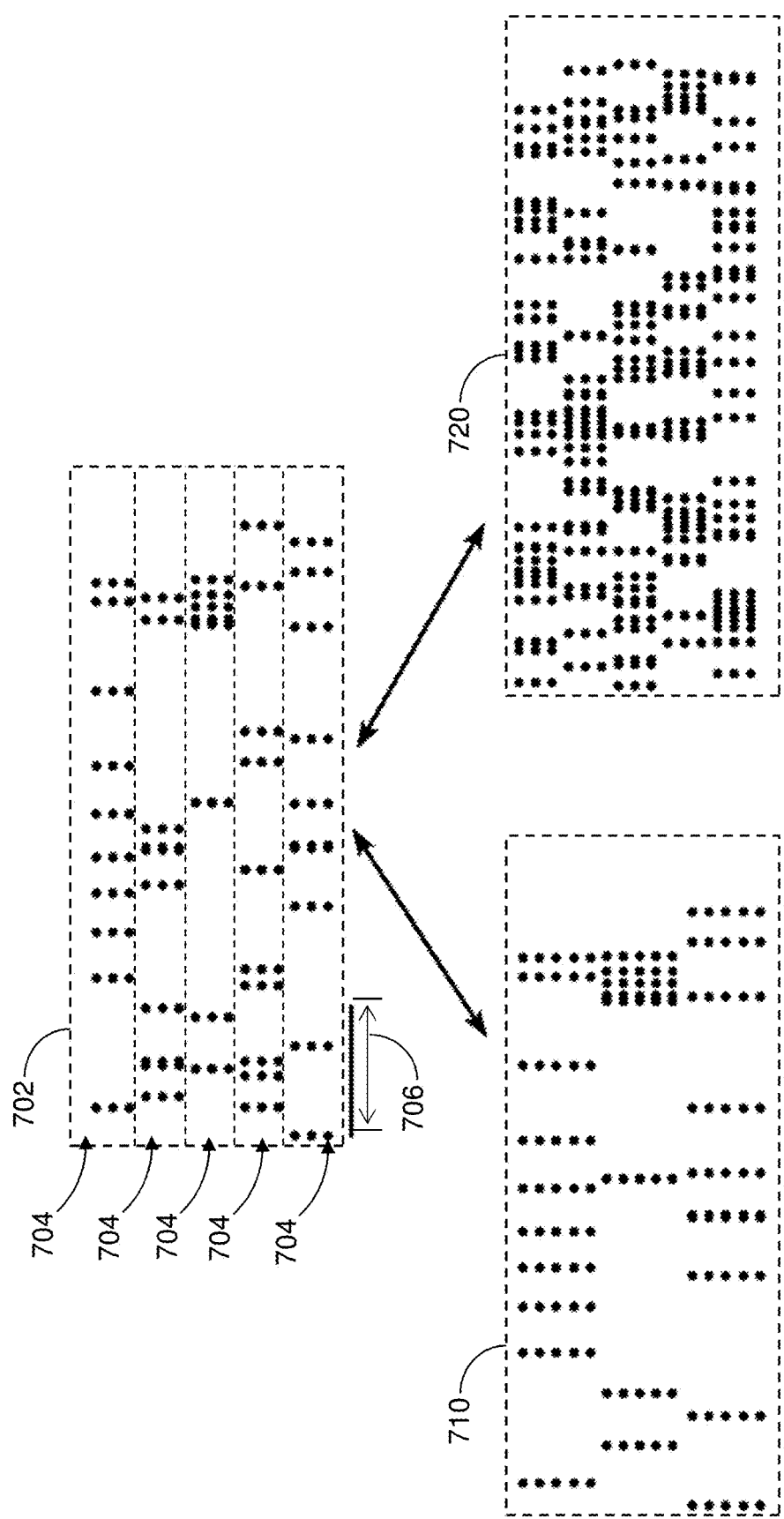
FIG. 7A is a diagram of programmable parameters regarding the properties of asynchronous SCS according to at least one embodiment.

FIG. 7A is a diagram of programmable stimulation parameters regarding the properties of asynchronous SCS according to at least one embodiment. Programmable parameters include but are not limited to the number of random SCS pulse trains, the distribution of electrodes/inputs to which random SCS pulse trains are delivered, and the statistical properties of the random SCS pulse trains (e.g., distribution of interpulse intervals, average frequency). In pulse train combinations 702, a base of ten pulses per second in five groups 704 is represented. A time interval 706 of two hundred milliseconds represents the time scale in the pulse train combinations 702, 710, and 720 in FIG. 7A. In pulse train combinations 710, the number of patterns delivered and the proportions of inputs/pattern are changed. In pulse train combinations 720, the statistical properties of patterns and equivalent pattern frequency are changed.

Figure 7B:
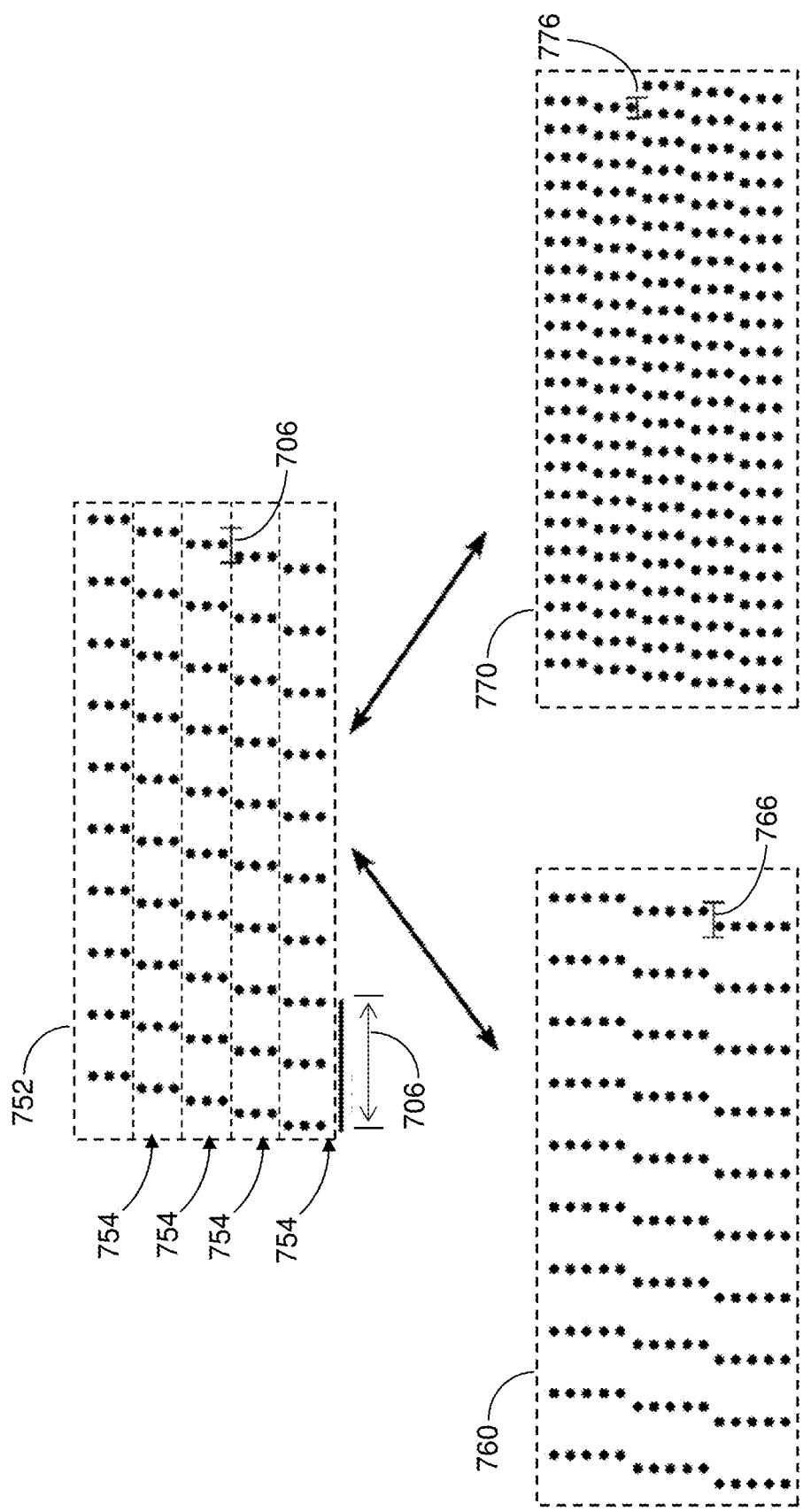
FIG. 7B is a diagram of programmable parameters of staggered SCS according to at least one embodiment.

FIG. 7B is a diagram of programmable stimulation parameters of staggered SCS, including, but are not limited to the number of staggered SCS pulse trains, the distribution of electrodes/inputs to which staggered SCS pulse trains are delivered, the frequency of the pulse train, and the percentage of the interpulse interval by which staggered pulse trains are offset relative to each other. In pulse train combinations 752, a base of ten pulses per second in five groups 754 is represented with 20% IPI stagger 756 between groups. The time interval 706 of two hundred milliseconds represents the time scale in the pulse train combinations 752, 760, and 770 in FIG. 7B. In pulse train combinations 760, the number of patterns delivered and the proportions of inputs/pattern are changed, and a 20% IPI stagger 766 between groups is shown. In pulse train combinations 770, the average frequency and percentage IPI stagger are changed, and a 10% IPI stagger 776 between groups is shown.

In at least one embodiment, SCS is carried out via an algorithm within a spinal cord stimulation pulse generator device or as a software program carried out on a remote computer, tablet, smartphone, controller, or similar device that may be used to configure a programmable pulse generator device. An on-board controller will deliver random SCS or staggered SCS, either pre-loaded or stored in memory or generated on-board the device, through different output channels to distinct contacts on the spinal cord stimulation electrode. By virtue of stimulation through multiple contacts, different or overlapping populations of axons traversing the dorsal column will be activated by distinct random or staggered pulse trains, resulting in greater suppression of the neurons responsible for transmitting nociceptive information to the brain than possible through single frequency SCS. Key parameters of random or staggered SCS, including but not limited to the equivalent average stimulation frequencies of the pulse trains, the number of distinct random/staggered pulse trains to deliver, the proportion of electrode contacts receiving each pulse train, the statistical characteristics of the random SCS, the percentage(s) of the IPI by which pulse trains are staggered, and the electrodes through which these frequencies are delivered. These key parameters can be input by either a physician or a patient through a user interface, or the device can be pre-programmed with specific configurations of random or staggered SCS. Equivalent stimulation frequencies delivered by the device may be delivered within clinically used ranges (e.g. 10-150 Hz) or at higher frequencies greater than 150 Hz. In addition, the device may be configured to deliver random SCS and constant frequency staggered SCS simultaneously through distinct electrode contacts. The algorithm could be toggled on and off (e.g. between random SCS, staggered SCS, and cfSCS) by either the patient or the physician, or it can be coupled to an internal feedback-driven algorithm for automatic control or optimization.

Figure 8A:
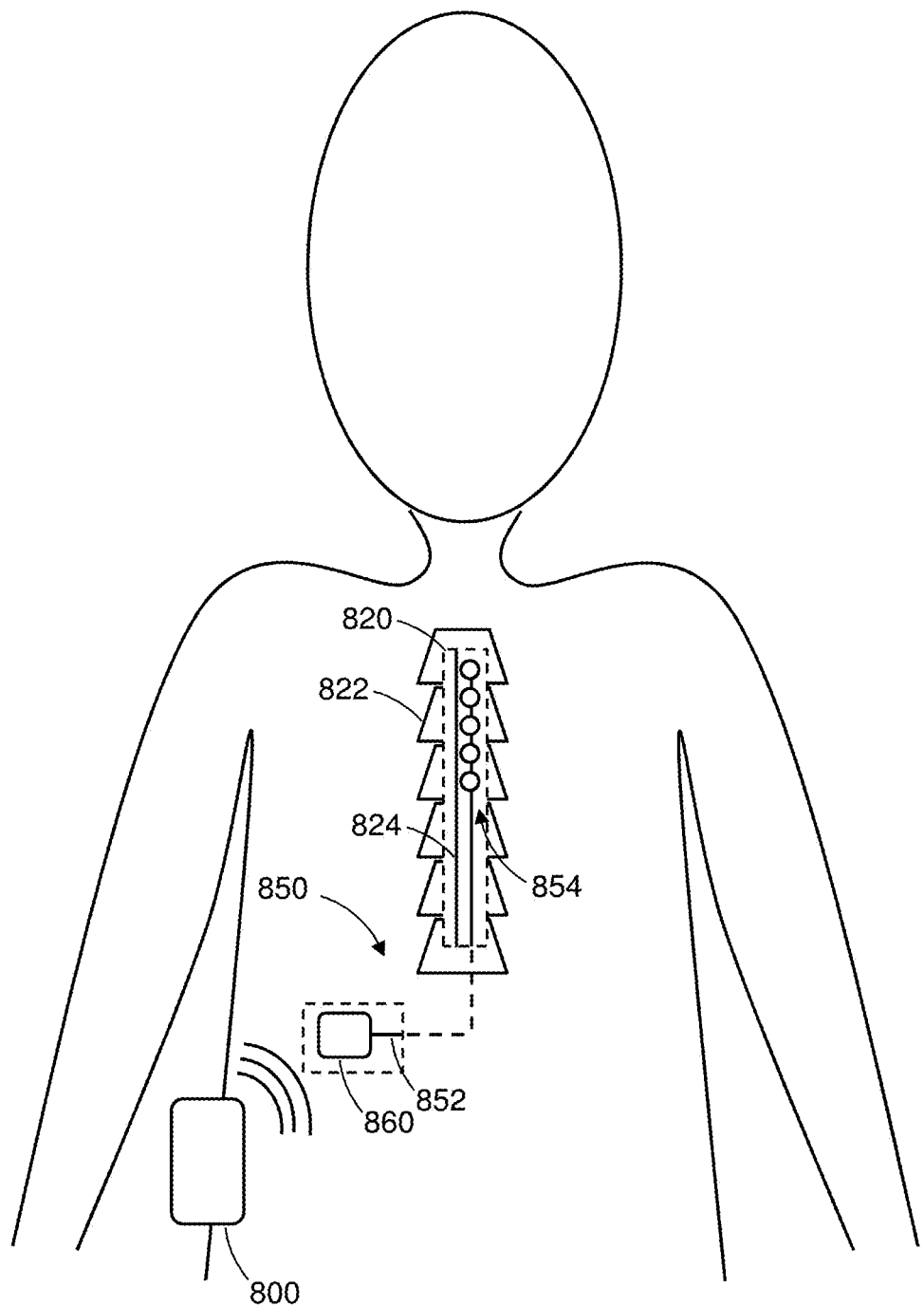
FIG. 8A is an illustration of a remote control device in use to program an SCS device according to at least one embodiment.
Figure 8B:
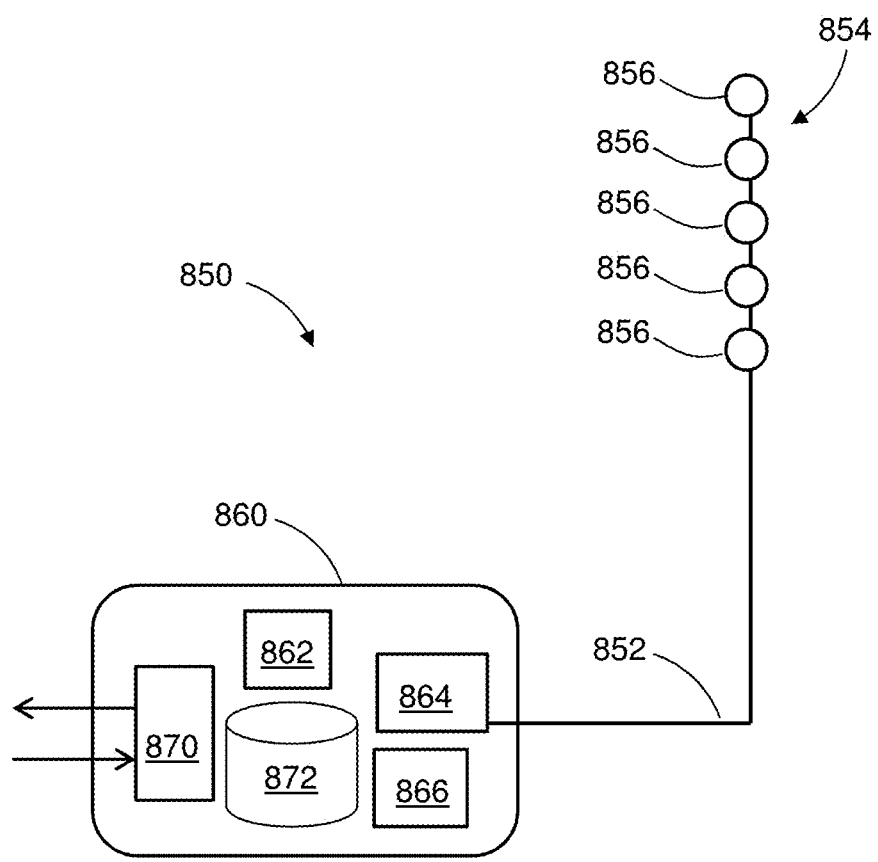
FIG. 8B is a block diagram of the SCS device of FIG. 8A.

An SCS system according to at least one embodiment is provided at least in part by a remote control device to program an SCS device. FIG. 8A is an illustration of a remote control device 800 in use to program the SCS device 850 according to at least one embodiment. FIG. 8B is a block diagram of the SCS device 850 of FIG. 8A.

Figure 9:
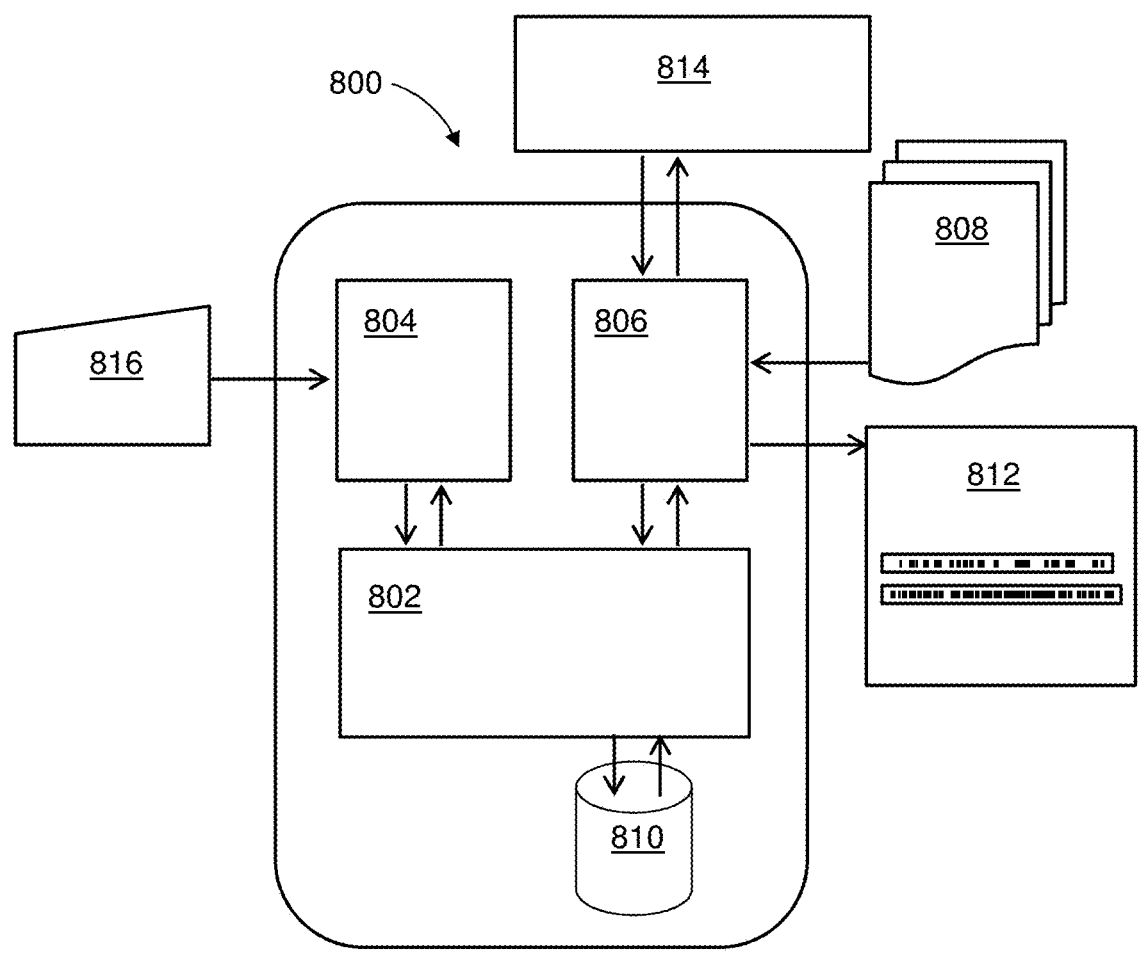
FIG. 9 is a block diagram of the remote control device of FIG. 6A.

FIG. 9 is a block diagram of the remote control device 800 of FIG. 6A. The remote control device 800 is shown in FIG. 9 as a stand-alone remote electronic device including of an internal processor 802, a user interface 804, and wired or wireless input/output ports 806 that are capable of communicating with the SCS device 850 (FIGS. 8A-8B). The internal processor 802 (FIG. 9) is capable of downloading, uploading, storing in a storage device 810, and running computer codes and other data content necessary for the generation of stimulation patterns and the transmission of such patterns to the SCS device 850. For example, the internal processor 802 sends and receives temporal pattern information and data to and from an external computer/database 814. The device 800 can receive SCS device data 808 and send SCS device pattern data 812. The stimulation patterns may be used by the SCS device to deliver stimulation. The internal processor 802 can either be custom-designed for this purpose and as part of a stand-alone device as illustrated in FIG. 8A. Other embodiments can be realized as a program on a computer, laptop computer, smartphone, personal desktop assistant (PDA), tablet, or other electronic device capable of remotely communicating with and controlling an SCS device pre- or post-implantation.

The user interface 804 (FIG. 9) receives user inputs 816 such as user commands and displays data to the user, such as the current patterns and combinations being delivered and/or measured biological indicators of pain such as but not limited to the firing rate of WDR neurons, and permits the user to select or vary the temporal pattern to be output by the device through a built-in hardware interface such as a touch screen, buttons/keyboard, and/or voice command.

Advantageously, the user interface 804 may allow the user to configure which active electrode contact(s) will deliver which temporal pattern(s) and/or frequencies. Communication with the SCS device 850 or an external system may occur through a direct wired link or wirelessly through the use of radiofrequency (RF) transmission, optical communication, Bluetooth, a wireless local area network (WLAN), or similar protocol. The remote control device 800 may send information or programming instructions to the SCS device 850 and receive information from the SCS device 850 regarding the current stimulation parameters such as the pattern(s) being delivered through one or more specific electrode contacts and information regarding the state of the patient, such as a neural signal corresponding to the patient's pain level.

FIG. 8A also illustrates an anatomic view of the SCS device 850 implanted to stimulate targeted neurological tissue of a human subject in accordance with at least one embodiment. The subject may be suffering from a neurological disorder, such as chronic pain or other condition. FIG. 8B is a block diagram of the SCS device of FIG. 8A. The SCS device 850 includes an electrical cord 852 and an array 854 of multiple electrodes 856. Five electrodes 856 are expressly shown but any number of electrodes can be included. The electrode array 854 is shown operatively positioned in FIG. 8A in the epidural space 820 of a vertebral column 822 of the subject. The electrode array 854 is positioned at the site of nerves that are the targets of stimulation, e.g., along the spinal cord 824. Alternatively, the electrode array 854 may be suitably positioned in any other location for desired electrical stimulation of targeted neurological tissue. The cord 852 may include multiple lines or leads such that different or the same electrical signals can be provided to the electrodes 856.

The SCS device 850 includes a control module 860 from which the cord 852 extends to any desired treatment location. As shown in FIG. 8A, the control module 860 of the SCS device 850 may be carried by the subject, for example in a pocket or specially adapted pouch, or may be suitably implanted within the subject such as, but not limited to, implantation within the abdomen or other body portion. The electrical cord 852 is operatively connected to an output of the control module 860 to deliver stimuli patterns to the desired subject via the electrode array 854.

As shown in FIG. 8B, the control module 860 of the SCS device 850 includes a local controller 862, a pulse generator 864, a power source 866, an input/output device 870, and a memory storage device 872. The local controller 862 may include a processor that runs software, firmware, or combinations thereof, for example stored on the memory storage device 872, for implementing functionality described herein. The controller 862 is operatively connected to the pulse generator 864 for controlling the pulse generator to generate electrical signals for applying patterns of electrical stimulation to targeted neurological tissue. The output signals of the pulse generator are conveyed by the electrical cord 852 to the electrode array 854 for electrical stimulation at targeted neurological tissue. The power source 866, such as a battery, supplies power to the local controller 862 and the pulse generator 864 and any other local devices as needed. The control module 860 may communicate with the remote control device 800 via the input/output device 870 by any suitable communication link (e.g., a wired, wireless, or optical communication link). The communication link may also facility battery recharging.

Particular embodiments described above relate particularly to electrical stimulation using electrodes that convert or convey electrical inputs to deliver electrical stimulation. Other stimulation modes and devices are also within the scope of these descriptions. For example, optical stimulation or modulation of the activity of dorsal column fibers can be applied by optical transducers. For further examples: acoustic (i.e., ultrasound) stimulation or modulation of the activity of dorsal column fibers can be applied by acoustic or ultrasonic transducers; thermal stimulation or modulation of the activity of dorsal column fibers can be applied by thermal transducers; and magnetic stimulation or modulation of the activity of dorsal column fibers can be applied by magnetic transducers.

A transducer converts or conveys energy to deliver stimulation. In the optical transducer example, an optical transducer converts an electrical signal or conveys a light signal and delivers optical stimulation. In the acoustic or ultrasonic example, an acoustic or ultrasonic transducer converts an electrical signal or conveys a sonic signal and delivers acoustic or ultrasonic stimulation. In the thermal example, a thermal transducer converts an electrical signal or conveys a heat signal and delivers thermal stimulation. In the magnetic example, and a magnetic transducer converts an electrical signal or conveys a magnetic signal and delivers magnetic stimulation.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A system for delivering electrical pulse stimulation, the system comprising:
   a control device configured to provide programming of intermittent, temporal pulse patterns; and
   a stimulation device comprising a control module, multiple electrodes in an array in electrical communication with the control module, and an input device intermittent communication configured to communicate with the control device to receive the programming, the stimulation device configured to deliver respective asynchronous temporal patterns of electrical stimulation pulses to the multiple electrodes according to the programming,
   wherein each respective asynchronous temporal pattern of electrical stimulation pulses activates a different subpopulation of targeted neurological tissue of a subject, and
   wherein the control module is configured to deliver the asynchronous temporal patterns by offsetting delivery of some pulse patterns relative to other pulse patterns.

2. The system for delivering electrical pulse stimulation according to claim 1, wherein the programming comprises instructions such that at least some of the patterns delivered comprise regular temporal patterns each having a respective constant inter-pulse interval.

3. The system for delivering electrical pulse stimulation according to claim 2, wherein the constant inter-pulse intervals are about the same.

4. The system for delivering electrical pulse stimulation according to claim 3, wherein offsetting delivery of some pulse patterns relative to other pulse patterns includes offsetting delivery by a time delay, wherein the time delay is approximately a percentage of the constant inter-pulse intervals.

5. The system for delivering electrical pulse stimulation according to claim 3, wherein offsetting delivery of some pulse patterns relative to other pulse patterns includes offsetting delivery by a time delay, wherein the temporal pulse pattern programming comprises instructions such that at least some of the patterns delivered differ from others of the patterns delivered only by the time delay such that the patterns are staggered.

6. The system for delivering electrical pulse stimulation according to claim 3, wherein offsetting delivery of some pulse patterns relative to other pulse patterns includes offsetting delivery by a time delay, wherein the programming comprises instructions such that some of the patterns delivered differ from others of the patterns according to time delays that vary.

7. The system for delivering electrical pulse stimulation according to claim 1, wherein the programming comprises instructions such that at least some of the patterns delivered comprise non-regular temporal patterns each having respective varying inter-pulse intervals.

8. The system for delivering electrical pulse stimulation according to claim 7, wherein offsetting delivery of some pulse patterns relative to other pulse patterns includes offsetting delivery by a time delay, wherein the programming comprises instructions such that at least some of the patterns delivered differ from others of the patterns delivered only by the time delay such that the patterns are staggered.

9. The system for delivering electrical pulse stimulation according to claim 1, wherein the programming comprises instructions such that:

at least some of the patterns delivered comprise regular temporal patterns each having a respective constant inter-pulse interval; and at least some of the patterns delivered comprise non-regular temporal patterns each having respective varying inter-pulse intervals.

10. The system for delivering electrical pulse stimulation according to claim 9, wherein offsetting delivery of some pulse patterns relative to other pulse patterns includes offsetting delivery by a time delay, wherein the programming comprises instructions such that at least some of the patterns delivered differ from others of the patterns delivered only by the time delay such that the patterns are staggered.

11. The system for delivering electrical pulse stimulation according to claim 1, wherein the programming comprises instructions such that at least some of the patterns delivered are random.

12. The system for delivering electrical pulse stimulation according to claim 1, wherein the control device comprises a remote control device configured to at provide the programming, and the input device of the stimulation device is configured to wirelessly communicate with the remote control device to receive the programming.

13. The system for delivering electrical pulse stimulation according to claim 12, wherein the remote control device is configured to generate or store the programming.

14. A method of delivering electrical stimulation comprising:

delivering asynchronous temporal patterns of electrical stimulation pulses to respective electrodes of an array of electrodes or respective transducers of an array of transducers, wherein delivering the asynchronous temporal patterns includes offsetting delivery of some pulse patterns relative to other pulse patterns, and wherein each respective asynchronous temporal pattern of electrical stimulation pulses activates a different sub-population of targeted neurological tissue of a subject.

15. The method of delivering electrical stimulation according to claim 14, wherein at least some of the patterns delivered comprise regular temporal patterns each having a respective constant inter-pulse interval.

16. The method of delivering electrical stimulation according to claim 14, wherein offsetting delivery of some pulse patterns relative to other pulse patterns includes offsetting delivery by a time delay, wherein at least some of the patterns delivered differ from others of the patterns delivered only by the time delay such that the patterns are staggered.

17. The method of delivering electrical stimulation according to claim 14, wherein offsetting delivery of some pulse patterns relative to other pulse patterns includes offsetting delivery by a time delay, wherein the deliveries of at least some of the patterns delivered differ from others of the patterns delivered according to time delays that vary.

18. The method of delivering electrical stimulation according to claim 14, wherein at least some of the patterns delivered comprise non-regular temporal patterns each having respective varying inter-pulse intervals.

19. The method of delivering electrical stimulation according to claim 14, wherein:

at least some of the patterns delivered comprise regular temporal patterns each having a respective constant inter-pulse interval; and at least some of the patterns delivered comprise non-regular temporal patterns each having respective varying inter-pulse intervals.

20. The method of delivering electrical stimulation according to claim 14, wherein at least some of the patterns delivered comprise non-regular varying temporal patterns.

21. A remote control device configured to provide programming of intermittent asynchronous temporal pulse patterns to a stimulation device that comprises an array of electrodes and delivers temporal patterns of electrical stimulation pulses to the electrodes according to the programming, wherein the stimulation device is configured to deliver the asynchronous temporal patterns by offsetting delivery of some pulse patterns relative to other pulse patterns, and wherein each respective asynchronous temporal pattern of electrical stimulation pulses activates a different sub-population of targeted neurological tissue of a subject.

22. The remote control device of claim 21, wherein at least some of the patterns are designed or optimized using an internal feedback driven algorithm.

* * * * *